(12) United States Patent
Van Dyke

(10) Patent No.: US 7,517,572 B2
(45) Date of Patent: Apr. 14, 2009

(54) COMPOSITE WEB

(75) Inventor: Wendy L. Van Dyke, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 472 days.

(21) Appl. No.: 11/116,655

(22) Filed: Apr. 27, 2005

(65) Prior Publication Data

US 2006/0246248 A1 Nov. 2, 2006

(51) Int. Cl.
*B32B 3/10* (2006.01)
*A61F 13/62* (2006.01)

(52) U.S. Cl. .............................. 428/43; 428/99; 206/390

(58) Field of Classification Search .................. 428/43, 428/99, 136; 24/442; 206/390; 156/271, 156/270
See application file for complete search history.

(56) References Cited

U.S. PATENT DOCUMENTS

| | | | | |
|---|---|---|---|---|
| 3,143,208 A | * | 8/1964 | Sizemore, Jr. ................ 428/43 |
| 3,299,440 A | * | 1/1967 | Grable ........................ 206/390 |
| 3,578,155 A | * | 5/1971 | Small et al. .................... 156/70 |
| 4,037,602 A | | 7/1977 | Hawthorne | |
| 4,418,105 A | * | 11/1983 | Stratton ..................... 428/41.8 |
| 4,663,220 A | | 5/1987 | Wisneski et al. | |
| 4,704,116 A | | 11/1987 | Enloe | |
| 4,753,650 A | | 6/1988 | Williams | |
| 4,798,603 A | | 1/1989 | Meyer et al. | |
| 4,916,005 A | | 4/1990 | Lippert et al. | |
| 4,988,346 A | | 1/1991 | Pfefferkorn | |
| 5,114,781 A | | 5/1992 | Morman | |
| 5,116,662 A | | 5/1992 | Morman | |
| 5,176,668 A | | 1/1993 | Bernardin | |
| 5,192,606 A | | 3/1993 | Proxmire et al. | |
| 5,226,992 A | | 7/1993 | Morman | |
| 5,486,166 A | | 1/1996 | Bishop et al. | |
| 5,490,846 A | | 2/1996 | Ellis et al. | |
| 5,496,298 A | | 3/1996 | Kuepper et al. | |
| 5,509,915 A | | 4/1996 | Hanson et al. | |
| 5,645,542 A | | 7/1997 | Anjur et al. | |
| 5,883,028 A | | 3/1999 | Morman et al. | |
| 5,964,743 A | | 10/1999 | Abuto et al. | |
| 6,195,850 B1 | * | 3/2001 | Melbye et al. ................ 24/304 |
| 6,231,557 B1 | | 5/2001 | Krautkramer et al. | |
| 6,264,784 B1 | | 7/2001 | Menard et al. | |
| 6,362,389 B1 | | 3/2002 | Mcdowall et al. | |
| 6,552,245 B1 | | 4/2003 | Roessler et al. | |
| 2003/0032933 A1 | | 2/2003 | Sayama | |
| 2006/0247596 A1 | | 11/2006 | Van Dyke | |
| 2006/0247597 A1 | | 11/2006 | Hogan et al. | |

FOREIGN PATENT DOCUMENTS

| | | |
|---|---|---|
| EP | 0 217 032 B1 | 2/1992 |
| EP | 1 108 372 A1 | 6/2001 |
| EP | 1 240 881 A2 | 9/2002 |
| EP | 1 602 348 A1 | 12/2005 |
| WO | WO 01/88245 A2 | 11/2001 |
| WO | WO 03/051254 A2 | 6/2003 |

* cited by examiner

*Primary Examiner*—Alexander Thomas
(74) *Attorney, Agent, or Firm*—John L. Brodersen; Randall W. Fieldhack

(57) ABSTRACT

Disclosed is a composite web including a base web, a first web of fastener material, a first sinusoidal line of separation and a second sinusoidal line of separation. In one aspect, the composite web can be used to form components for absorbent articles.

20 Claims, 6 Drawing Sheets

COMPOSITE WEB

BACKGROUND OF THE INVENTION

The present invention relates to a composite web. More specifically, the invention relates to a composite web that can suitably be used to provide components for disposable absorbent articles.

Contemporary absorbent articles such as disposable diapers can include many components that can improve the fit of the article, the containment of the article, the appearance of the article or a combination of these characteristics. Examples of these components can include components that are typically elasticized, such as waist elastics, leg elastics, or containment flaps. Another example of such components are ears that extend outboard of the lateral edges of the article. Such ears may or may not be elasticized. For the most part, such components are often incorporated into the article during the production process by separating them from a composite web that includes the desired materials and performance characteristics for the components.

As can be readily appreciated, adding each of these components can increase the complexity of the production process due to added process steps and process equipment. Thus, while it is desirable to include components to enhance an article, adding these components also can increase waste and delay due to the increased complexity of the process and added process steps.

Thus, there is a need for a single composite web from which multiple added components may be obtained. Further, there is a need for a composite web that can provide the multiple components with a reduced amount of material waste. Still further, there is a need for a composite web that is capable of providing the components without requiring a complex process that can require complex equipment.

SUMMARY OF THE INVENTION

In one aspect, the present invention is directed to a composite web defining a lateral direction, longitudinal direction, a longitudinal centerline, a first composite web side edge a second composite web side edge opposed to the first composite web side edge, a first planar surface and a second planar surface opposite the first planar surface. The composite web includes a base web and a first web of fastener material disposed on the base web between the first and second composite web side edges and extending in the longitudinal direction. The composite web also includes a first sinusoidal line of separation extending in the longitudinal direction and passing through the base web. The composite web also includes a second sinusoidal line of separation laterally spaced from the first sinusoidal line of separation, extending in the longitudinal direction and passing through the base web.

In another aspect, the present invention is directed to a composite web defining a lateral direction, a longitudinal direction and a longitudinal centerline. The composite web includes a base web a first web of fastener material disposed on the base web and a first sinusoidal line of separation passing through the base web. The composite web also includes a second sinusoidal line of separation passing through the base web and a plurality of interconnecting lines of separation that extend from the first sinusoidal line of separation to the second sinusoidal line of separation and pass through the base web. The composite web also includes a plurality of first outboard lines of separation that extend from the first sinusoidal line of separation away from the longitudinal centerline and a plurality of second outboard lines of separation that extend from the second sinusoidal line of separation away from the longitudinal centerline. The first sinusoidal line of separation, the second sinusoidal line of separation, the plurality of interconnecting lines of separation, the first outboard lines of separation and the second outboard lines of separation are configured to form discrete components from the composite web free from any trim waste.

In yet another aspect, the present invention is directed to a composite web defining a lateral direction, a longitudinal direction and a longitudinal centerline. The composite web includes a base web, a first web of fastener material disposed on the base web and a first line of separation passing through the base web. The composite web also includes a second line of separation passing through the base web a plurality of interconnecting lines of separation that extend from the first line of separation to the second line of separation and pass through the base web. The composite web also includes a plurality of first outboard lines of separation that extend from the first line of separation away from the longitudinal centerline and a plurality of second outboard lines of separation that extend from the second line of separation away from the longitudinal centerline. The first line of separation, the second line of separation, the plurality of interconnecting lines of separation, the first outboard lines of separation and the second outboard lines of separation are configured to form discrete components from the composite web free from any trim waste.

In still yet another aspect, the present invention is directed to a method for making components suitable for an absorbent article from a composite web of material. The method includes providing a base web including a first web of fastener material disposed on the base web to form a composite web where the composite web defines a lateral direction and a longitudinal direction. The method also includes creating a first line of separation in the composite web passing through the base web and extending substantially in the longitudinal direction. The method also includes creating a second line of separation in the composite web passing through the base web and extending substantially in the longitudinal direction. The method also includes creating a series of interconnecting lines of separation in the composite web extending substantially in the lateral direction where the first sinusoidal separation, the second sinusoidal separation, and the interconnecting lines of separation combine to provide a plurality of components from the composite web without any remaining trim waste.

The above-mentioned and other aspects of the present invention will become more apparent, and the invention itself will be better understood by reference to the drawings and the following description of the drawings.

BRIEF DESCRIPTION OF THE DRAWINGS

Corresponding reference characters indicate corresponding parts throughout the drawings.

Definitions

Figure 1:
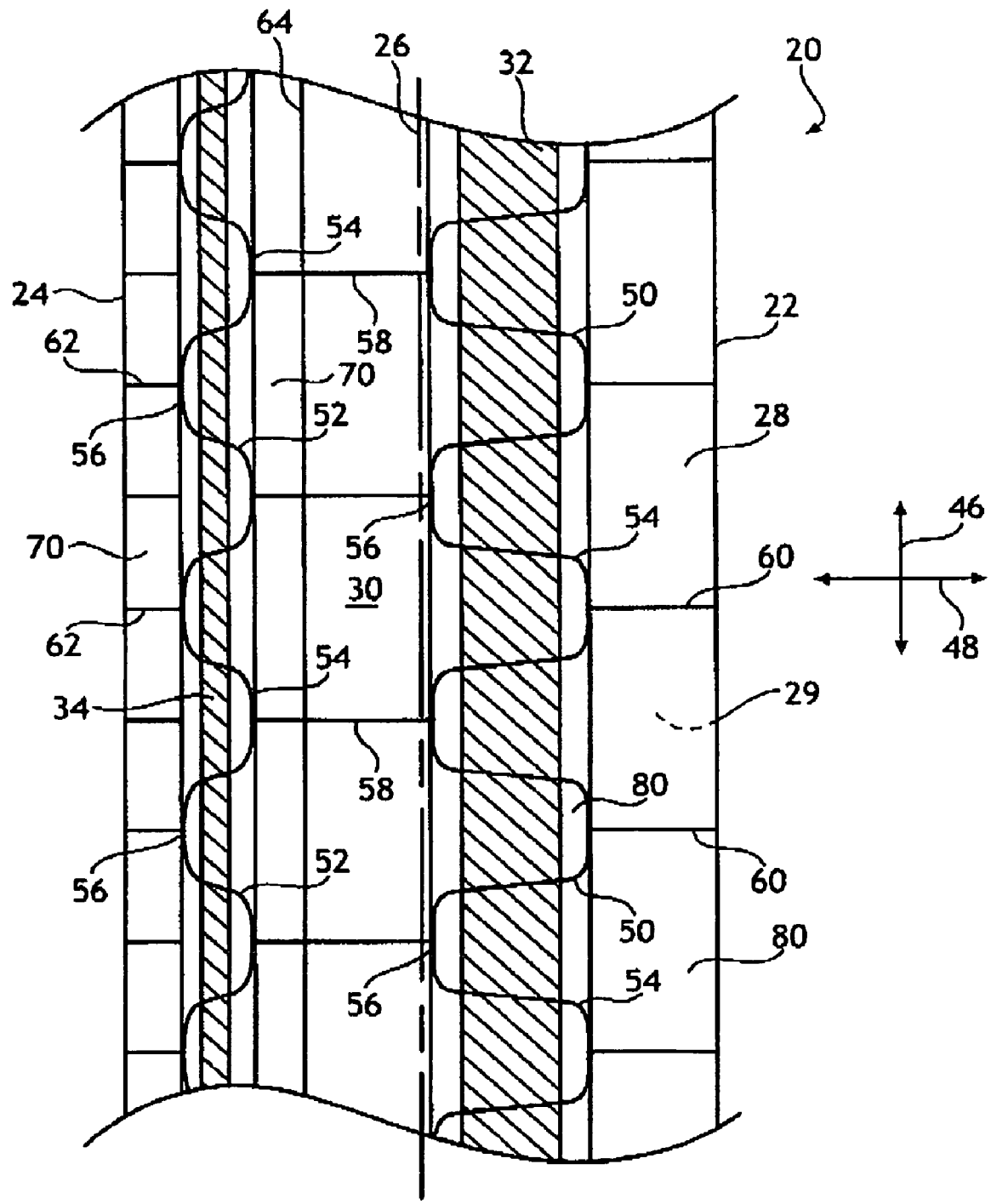
FIG. 1 representatively illustrates an example of a composite web of the present invention.

Within the context of this specification, each term or phrase below includes the following meaning or meanings:

"Attach" and its derivatives refer to the adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end user.

"Connect" and its derivatives refer to the adhering, bonding, attaching, sewing together, or the like, of two elements. Two elements will be considered to be connected together when they are integral with one another or connected directly to one another or indirectly to one another, such as when each is directly connected to intermediate elements. "Connect" and its derivatives include permanent, releasable, or refastenable connection.

"Complementary shape" when used in the context to describe components for absorbent articles (for example, diaper ears) means that a pair of the components are configured such that when they are nested with each other, a minimum of gapping will exist between the components. Thus, the pair of components could be cut from the same web of material without any trim waste material resulting from spacing between the components.

"Disposable" refers to articles which are designed to be discarded after a limited use rather than being laundered or otherwise restored for reuse.

The terms "disposed on," "disposed along," "disposed with," or "disposed toward" and variations thereof are intended to mean that one element can be integral with another element, or that one element can be a separate structure bonded to or placed with or placed near another element.

"Elastic," "elasticized," "elasticity," and "elastomeric" mean that property of a material or composite by virtue of which it tends to recover its original size and shape after removal of a force causing a deformation. Suitably, an elastic material or composite can be elongated by at least 25 percent (to 125 percent) of its relaxed length and will recover, upon release of the applied force, at least 40 percent of its elongation.

"Extensible" refers to a material or composite which is capable of extension or deformation without breaking, but does not substantially recover its original size and shape after removal of a force causing the extension or deformation. Suitably, an extensible material or composite can be elongated by at least 25 percent (to 125 percent) of its relaxed length.

"Fiber" refers to a continuous or discontinuous member having a high ratio of length to diameter or width. Thus, a fiber may be a filament, a thread, a strand, a yarn, or any other member or combination of these members.

"Join" and its derivatives refer to the adhering, bonding, sewing together, or the like, of two separate elements. Two elements will be considered to be joined together when they are joined directly to one another or indirectly to one another, such as when each is directly joined to intermediate elements. "Join" and its derivatives include permanent, releasable, or refastenable joinder.

"Layer" when used in the singular can have the dual meaning of a single element or a plurality of elements.

"Liquid impermeable," when used in describing a layer or multi-layer laminate means that liquid, such as urine, will not pass through the layer or laminate, under ordinary use conditions, in a direction generally perpendicular to the plane of the layer or laminate at the point of liquid contact.

"Liquid permeable" refers to any material that is not liquid impermeable.

"Member" when used in the singular can have the dual meaning of a single element or a plurality of elements.

"Nonwoven" and "nonwoven web" refer to materials and webs of material that are formed without the aid of a textile weaving or knitting process. For example, nonwoven materials, fabrics or webs have been formed from many processes such as, for example, meltblowing processes, spunbonding processes, air laying processes, and bonded carded web processes.

"Repeat length" refers to the maximum length in the longitudinal direction of a component that may be formed from the composite web of the present invention.

"Sinusoidal" refers to a waveform pattern that includes alternating peaks and troughs. The pattern may be curvilinear or rectilinear or other shapes and still be sinusoidal. In addition, the peaks and troughs may plateau or they ultimately can reach a point.

"Stretchable" means that a material can be stretched, without breaking, by at least 25 percent (to 125 percent of its initial (unstretched) length) in at least one direction. Elastic materials and extensible materials are each stretchable materials.

"Superabsorbent material" refers to a water-swellable, water-insoluble organic or inorganic material capable, under the most favorable conditions, of absorbing at least about ten times its weight and, more desirably, at least about thirty times its weight in an aqueous solution containing about 0.9 weight percent sodium chloride.

These terms may be defined with additional language in the remaining portions of the specification.

DETAILED DESCRIPTION

Referring now to the drawings and in particular to FIG. 1, a composite web of the present invention is representatively illustrated in the form of a web from which complementary shaped front ears 70 and complementary shaped back ears 80 can be formed and is indicated in its entirety by the reference numeral 20. It should also be understood that the present invention can be suitably configured to produce other components or may be suitable for use with various other absorbent articles intended for personal wear, including but not limited to children's training pants, feminine hygiene products, incontinence products, medical garments, surgical pads and bandages and the like without departing from the scope of the present invention.

The composite web 20 defines a longitudinal direction 46 and a lateral direction 48 perpendicular to the longitudinal direction as shown in FIGS. 1-4. The composite web 20 further defines a first composite web side edge 22 and a second composite web side edge 24 opposite the first composite web side edge 22, each extending in the longitudinal direction 46, a longitudinal composite web centerline 26, a first planar surface 28 and a second planar surface 29 opposite the first planar surface 28.

The composite web 20 can include a base web 30 and a first web of fastener material 32 disposed on the base web 30. The first web of fastener material 32 can be disposed on the base web 30 between the first and second composite web side edges 22, 24. The composite web 20 can also optionally include a second web of fastener material 34 disposed on the base web 30 and laterally spaced from the first web of fastener material 32. Similar to the first web of fastener material 32, the second web of fastener material 34 may be disposed on the base web 30 between the first and second composite web side edges 22, 24. The first web of fastener material 32 and the second web of fastener material 34 can extend substantially in the longitudinal direction 46.

The base web 30 of the present invention can be provided by materials as are known in the art such as woven materials, nonwoven materials, or combinations thereof. In a particular aspect, at least a portion of the base web 30 is an elastomeric material capable of elongating in at least the lateral direction 46. Examples of a suitable elastomeric material for use in connection with the base web 30 are a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference in their entirety to the extent they are consistent (i.e., not in conflict) herewith.

As is known in the art, the base web 30 can optionally include nonstretchable materials or stretchable but inelastic materials. For example, the base web 30 can include various nonstretchable nonwovens such as a spunbond material, a spunbond/meltblown/spunbond (SMS) material or a bonded carded web. Alternatively, the base web 30 can include film materials that can be liquid impermeable or liquid permeable.

Figure 2:
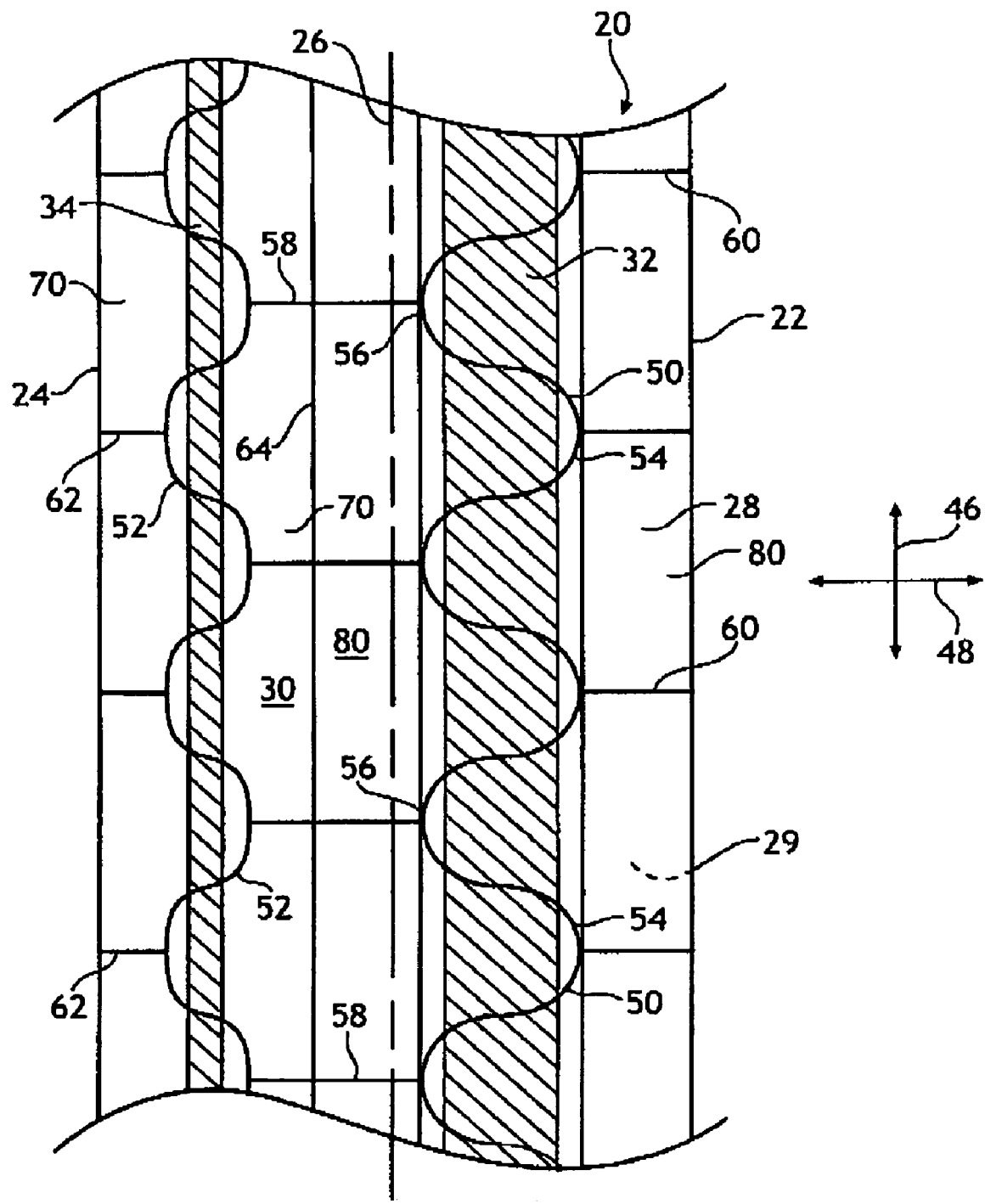
FIG. 2 representatively illustrates another example of a composite web of the present invention.
Figure 3:
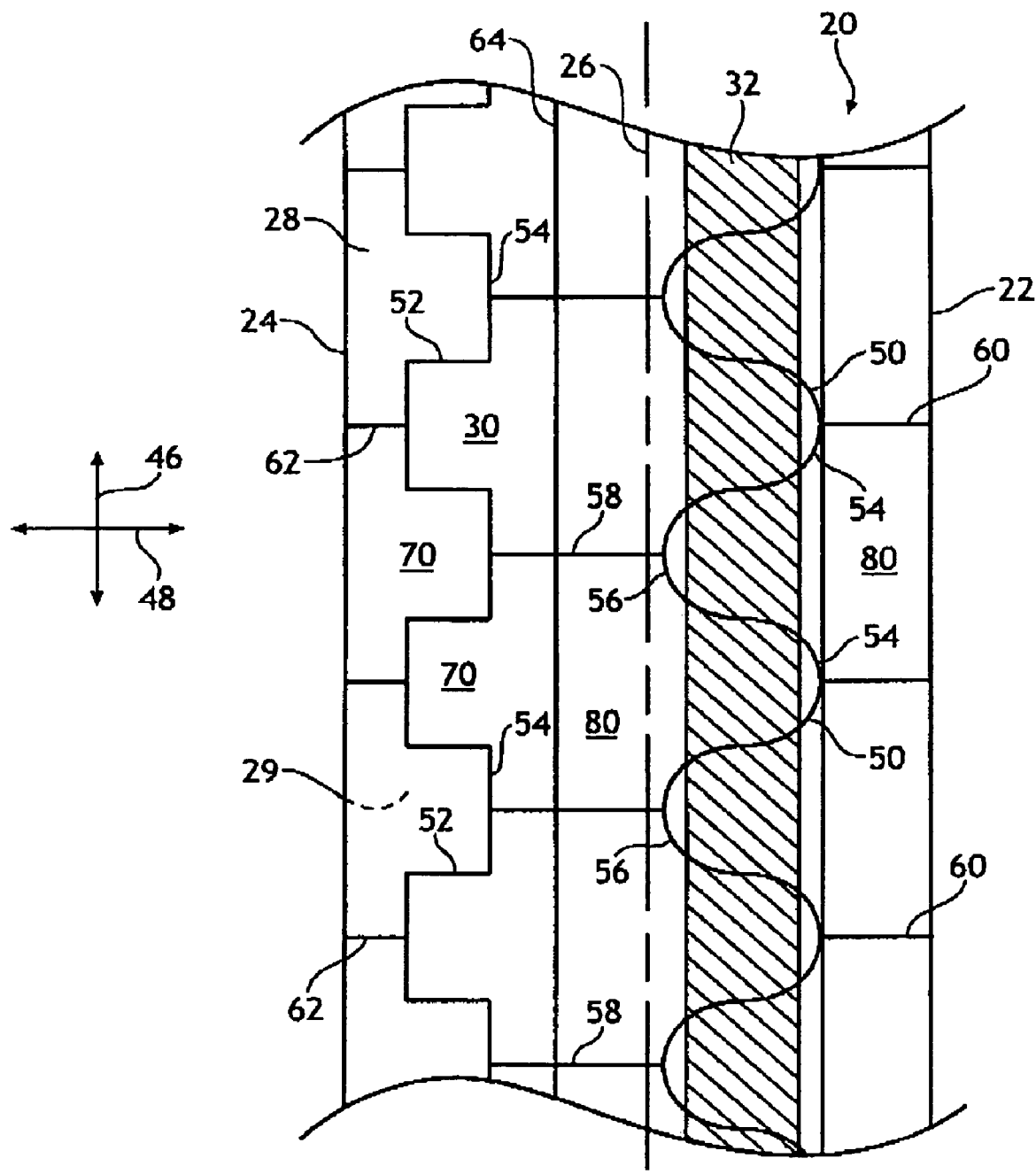
FIG. 3 representatively illustrates yet another example of a composite web of the present invention.
Figure 4:
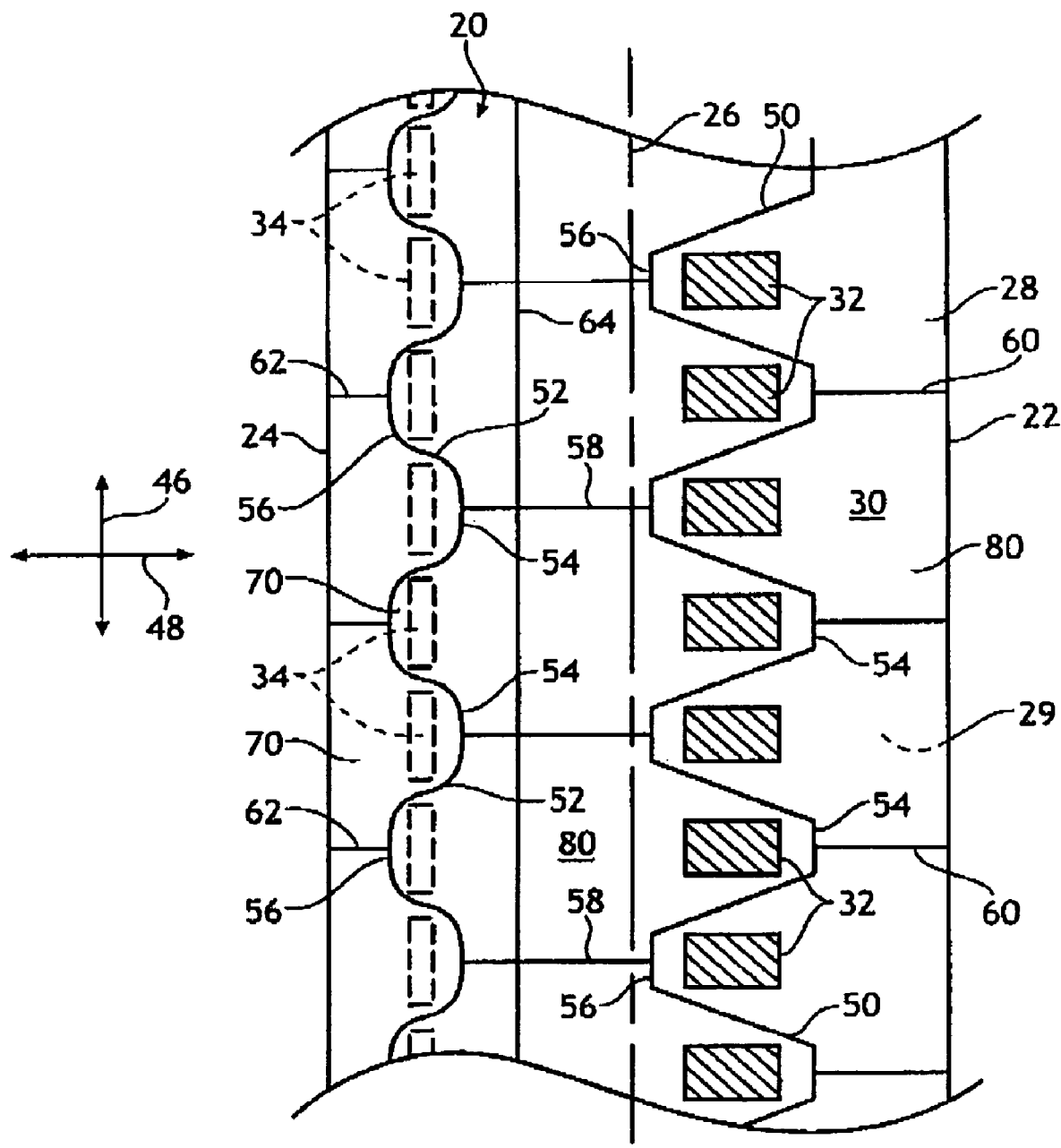
FIG. 4 representatively illustrates yet another example of a composite web of the present invention.

As representatively illustrated in FIG. 2, the base web 30 can be a substantially uniform, single layer of material (FIGS. 3 and 4). Alternatively, as representatively illustrated in FIGS. 1 and 2, the base web 30 can include multiple layers of materials extending in the lateral direction 48 that are attached together to provide the base web 30. Suitably, the base web 30 can be multiple materials to provide a variety of desired properties within the base web 30. Such a configuration can provide a base web 30 from which different complementary diaper components, such as complementary shaped front ears 70 and complementary shaped back ears 80, can be separated, with at least some of the components featuring different desired properties, such as stretchability, breathability, softness, durability and the like or combinations thereof.

Specifically, the base web 30 can be a combination of stretchable and nonstretchable materials. For example, the base web can include nonstretchable materials adjacent the composite web side edges 22, 24, while the base web 30 adjacent the longitudinal centerline 26 could be stretchable. Alternatively, as representatively illustrated in FIGS. 1 and 2, the base web 30 can include alternating layers of different materials, such as stretchable and non-stretchable materials. As can be readily appreciated by those of skill in the art, the properties that can be advantageously included within the base web 30 are not limited to stretchability. For example, different layers can be utilized to provide a desired level of breathability, liquid permeability, opacity, or durability and the like or combinations thereof. In particular aspects, it may be advantageous to attach fastener material to a non-stretchable portion of the base web 30.

The layers making up the base web 30 can be assembled in various ways as are known in the art. For example, the layers in the base web 30 can be assembled with adhesives, ultrasonic bonding, pressure bonding, thermal bonding, and the like or combinations thereof. Similarly, the first and second webs of fastener material 32 and 34 can be attached to the base web 30 in a manner as described above, or can be integrally formed with the base web 30. Alternatively, and as mentioned above, the base web 30 can be provided by a single layer of material.

In the various aspects of the present invention, the first web of fastener material 32 may be a continuous strip of material (FIGS. 1-3). Alternatively, the first web of fastener material 32 can be more than one discontinuous strip of material (i.e., multiple discrete pieces, FIG. 4). Similarly, the second web of fastener 34 material can be a continuous strip of material or can by more than one discontinuous strip of material (i.e., multiple discrete pieces). In aspects with a first and second web of fastener material 32, 34, they may each be continuous webs, discontinuous webs, or one may be continuous while the other may be discontinuous.

In aspects where the first and second webs of fastener material 32, 34 are discontinuous strips of material, the discontinuous strips of material of the first web of fastener material 32 can be positioned in an offset relationship with the discontinuous strips of material of the second web of fastener material 34. Alternatively, the discontinuous strips of material of the first web of fastener material 32 can be arranged to at least partially align with the discontinuous strips of material of the second web of fastener material 34, as representatively illustrated in FIG. 4.

Discontinuous strips of material from the first web of fastener material 32 are offset with discontinuous strips of material from the second web of fastener material 34 when an imaginary line drawn in the lateral direction 48 through a discrete strip of fastener material of the first web of fastener material 32 does not pass through a discrete strip of fastener material of the second web of fastener material 34. Conversely, discontinuous strips of material from the first web of fastener material 32 are aligned with discontinuous strips of material from the second web of fastener material 34 when an imaginary line drawn in the lateral direction 48 through a discrete strip of fastener material of the first web of fastener material 32 does pass through a discrete strip of fastener material of the second web of fastener material 34.

Further, the first and second webs of fastener material 32 and 34 may be disposed on the same surface 28 and 29 of the composite web or different surfaces 28 and 29 of the composite web. For example, in aspects that include a first and second web of fastener material 32 and 34, the first and second webs of fastener material 32 and 34 can both be disposed on the first planar surface 28. Alternatively, the first and second webs of fastener material 32 and 34 can both be disposed on the second planar surface 29. In yet another alternative, the first web of fastener material 32 can be disposed on the first planar surface 28 while the second web of fastener material 34 is disposed on the second planar surface 29 (FIG. 4), or vice versa. In aspects where the webs of fastener material 32 and 34 are on different surfaces 28 and 29 of the composite web 20, the components (such as ears 70 and 80) can be presented to the diaper 100 with the fastener material facing in opposite directions. This arrangement advantageously saves the added process step of having to flip one set of ears 70 or 80 where this configuration is desired, such as when the fastener material on one set of ears 70 or 80 is used to engage one surface of the diaper 100 while the other set of ears is used to engage an opposing surface of the diaper 100.

The first and second webs of fastener material 32 and 34 may include any fasteners suitable for absorbent articles, such as adhesive fasteners, cohesive fasteners, mechanical fasteners, or the like. Suitable mechanical fasteners can include interlocking geometric-shaped materials that are intended to engage another material such as hooks, bulbs, mushrooms, arrowheads, balls on stems, male mating components or the like. One specific example of a fastener material is VELCRO HTH 858 or VELCRO HTH 823 available from Velcro Industries B.V., Amsterdam, Netherlands.

The composite web 20 of the present invention can further include lines of separation. The lines of separation may be substantially linear, curvilinear or the like or combinations thereof. In particular, the composite web can include a first sinusoidal line of separation 50. As representatively illustrated in FIGS. 1-5, the first sinusoidal line of separation 50 can extend in the longitudinal direction 46 and pass at least through the base web 30. Optionally, the first sinusoidal line of separation 50 can also pass through the first web of fastener material 32 (FIG. 1-3), for example where the first web of fastener material 32 is a substantially continuous strip of fastener material. Alternatively, in configurations where the first web of fastener material is a series of multiple discrete pieces of fastener material, the first sinusoidal line of separation may fall within the longitudinal separation between the discrete pieces of fastener material (FIG. 4).

The composite web 20 can also include a second sinusoidal line of separation 52. For example, as representatively illustrated in FIGS. 1-4, the second sinusoidal line of separation 52 can be laterally spaced from the first sinusoidal line of separation 50 and extend in the longitudinal direction 46. Further, the second sinusoidal line of separation 52 may pass through at least the base web 30. In configurations where the composite web includes a second web of fastener material 34, the second sinusoidal line of separation 52 can also pass through the second web of fastener material 34 (FIG. 1-3), for example where the second web of fastener material 34 is a substantially continuous strip of fastener material. Alternatively, in configurations where the second web of fastener material 34 is a series of multiple discrete pieces of fastener material, the second sinusoidal line of separation 52 may fall within the longitudinal separation between the discrete pieces of fastener material (FIG. 4).

The sinusoidal lines of separation 50 and 52 of the present invention include alternating peak regions 54 and trough regions 56. Accordingly, the sinusoidal lines of separation 50, 52 can have various configurations to achieve this arrangement such as curvilinear (FIGS. 1-4), rectilinear (FIG. 3), or trapezoidal (FIG. 4), or combinations thereof (FIGS. 3 and 4). As such, each of the sinusoidal lines of separation 50 and 52 can define a plurality of peak regions 54 and a plurality of trough regions 56. Optionally, as representatively illustrated in FIGS. 1-4, the peak regions 54 of the first sinusoidal line of separation 50 can be aligned with trough regions 56 of the second sinusoidal line of separation 52. Alternatively, the peak regions 54 of the first sinusoidal line of separation 50 can be aligned with peak regions 54 of the second sinusoidal line of separation 52.

The composite web 20 of the present invention can also include a plurality of interconnecting lines of separation 58 that can extend from the first sinusoidal line of separation 50 to the second sinusoidal line of separation 52. As representatively illustrated in FIGS. 1-4, the interconnecting lines of separation 58 can extend substantially in the lateral direction 48 from the first sinusoidal line of separation 50 to the second sinusoidal line of separation 52. In a particular aspect, interconnecting lines of separation 58 can extend from the peak regions 54 in the first sinusoidal line of separation to the trough regions 56 in the second sinusoidal line of separation 52 (FIGS. 1-4). Alternatively, the interconnecting lines of separation 58 can extend from the peak regions 54 in the second sinusoidal line of separation 52 to the trough regions 56 in the first sinusoidal line of separation 50.

The composite web 20 can further include outboard lines of separation. For example, as representatively illustrated in FIGS. 1-4, first outboard lines of separation 60 can extend from the first sinusoidal line of separation 50 away from the longitudinal centerline 26 to the first composite web side edge 22 that is proximate the first sinusoidal line of separation 50. In addition, the composite web 20 can also include second outboard lines of separation 62 extending from the second sinusoidal line of separation 52 away from the composite web centerline 26 to the second composite web side edge 24 that is proximate the second sinusoidal line of separation 52 (FIGS. 1-4). In a particular aspect, the first and second outboard lines of separation 60, 62 can extend in from the first and second sinusoidal lines of separation 50, 52 to the first and second composite web side edges 22, 24, respectively, in a substantially lateral direction 46.

The composite web 20 can further include dividing lines of separation 64. For example, as representatively illustrated in FIGS. 1-4, the dividing line of separation 64 can extend substantially in the longitudinal direction 46, and may optionally be parallel to one or both of the composite web side edges 22, 24. The dividing line of separation 64 can separate the two pairs of complementary components, such as front and back ears 70, 80, from each other on the composite web 20. Accordingly, the dividing line of separation 64 can be located between the first and second sinusoidal lines of separation 50, 52.

The various lines of separation 50, 52, 58, 60, 62, 64 of the present invention can be provided in a variety of ways as are known in the art. For example, the lines of separation 50, 52, 58, 60, 62, 64 can be continuous cuts that completely sever the various layers of the base web 30 and optionally the first and/or second web of fastener material 32 or 34. Alternatively, the lines of separation 50, 52, 58, 60, 62, 64 can be provided by a line of weakness such as a score line or a series of perforations. In such an aspect, the lines of separation 50, 52, 58, 60, 62, 64 can be provided in the composite web 20 with the composite web 20 later being separated into components such as front and back ears 70, 80 when desired. In yet another alternative, the various lines of separation 50, 52, 58, 60, 62, 64 of the composite web 20 of the present invention can be provided by a combination of continuous cuts, lines of weakness, or the like.

The various lines of separation 50, 52, 58, 60, 62, 64 of the present invention can be provided or created in the composite web 20 in a number of ways as are known in the art. For example, a die cutting device can provide some or all of the lines of separation 50, 52, 58, 60, 62, 64. Alternatively, a watercutting device or an ultrasonic cutting device, or the like can be used. Optionally, a combination of the above methods can be used. Further, the lines of separation 50, 52, 58, 60, 62, 64 can be created in stages by different devices or simultaneously by a single device.

Accordingly, the various lines of separation 50, 52, 58, 60, 62, 64 can be configured to provide various absorbent article components from the composite web 20. For example, front ears 70 and back ears 80 can be provided by the composite web 20. Specifically, the first sinusoidal line of separation 50, the second sinusoidal line of separation 52, the interconnecting lines of separation 58, the outboard lines of separation 60, 62, and the dividing line of separation 64 can be configured to form complementary shaped components from the composite web 20 that can be used in connection with absorbent articles such as a diaper 100. In particular, the complementary shaped components can be formed from the composite web 20 free of any trim waste. In a particular aspect and as will be described in greater detail below, the various lines of separation 50, 52, 58, 60, 62, 64 can be configured to form a pair of complementary shaped front ears 70 and a pair of complementary shaped back ears 80 from the composite web 20, free from any trim waste, and that can be configured to be joined to a diaper 100. That is, after separating the ears 70, 80 from the web 20, there is no left over composite web material that must be discarded, recycled or otherwise dealt with in the process, thereby advantageously reducing material cost and process complexity. Moreover, two sets of components, the front ears 70 and the back ears 80, can be provided from a single web of material. As such, the process is potentially further simplified by providing the capability of obtaining two sets of components from one process.

Thus, as can be readily appreciated, the present invention can also provide a method for making components suitable for an absorbent article, such as the diaper 100. The base web 30 can be provided to a diaper converting process using unwind equipment commonly known in the art. The base web 30 can include at least a first web of fastener material 32 and optionally the second web of fastener material 34 before being provided to the converting process. Alternatively, the first and second webs of fastener material 32 and 34 can be disposed on the base web 30 as it is being unwound into the converting process.

Using the methods described above, the various lines of separation 50, 52, 58, 60, 62, 64 can be created in the composite web 20 to provide a plurality of components, such as ears 70 and 80 from the composite web 20, suitably without any trim waste. In a particular aspect, the composite web can be separated into four webs, for example at the first and second sinusoidal lines of separation 50, 52 and at the dividing line of separation 64 before being separated into a plurality of front and back ears 70, 80.

Figure 5:
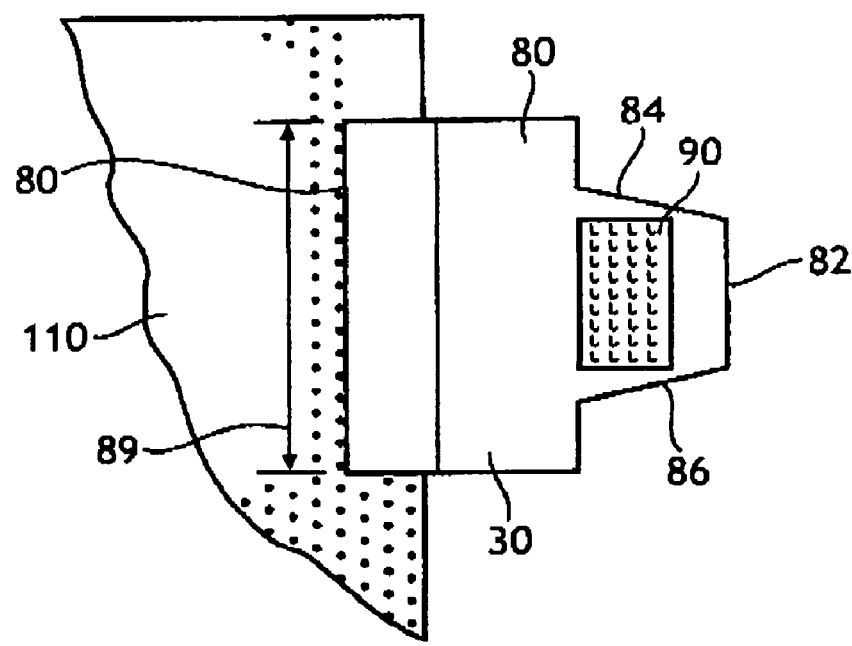
FIGS. 5 and 6 representatively illustrate examples of back ears and front ears, respectively, that can be formed from the composite web of the present invention.
Figure 6:
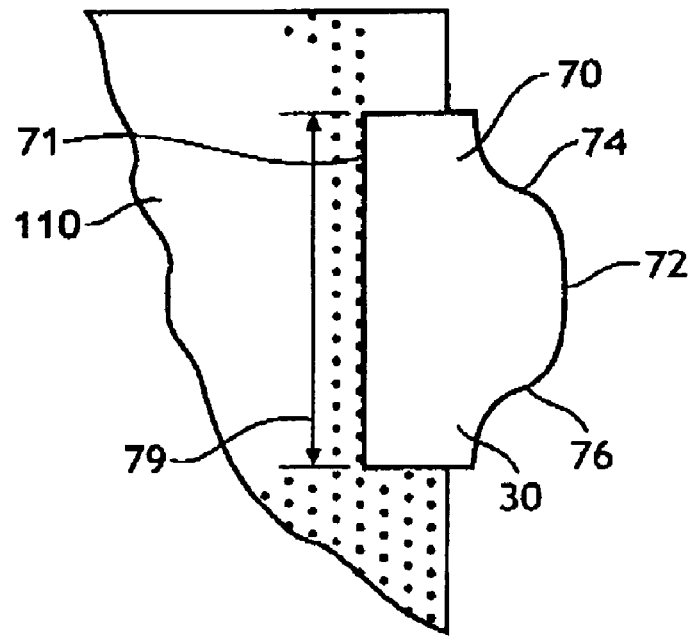
Figure 7:
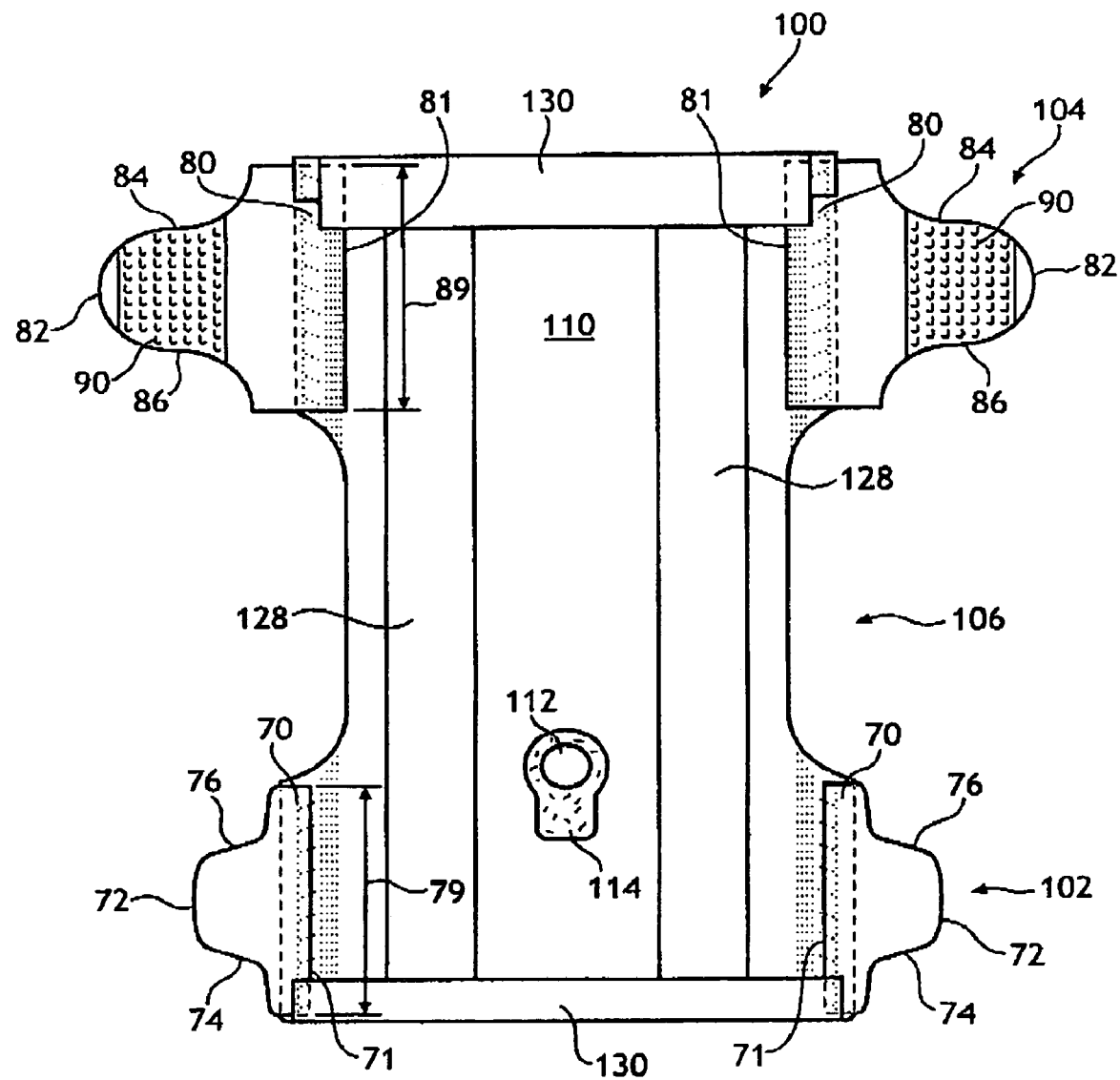
FIG. 7 representatively illustrates a plan view of a diaper in an unfastened, stretched and laid flat condition, and showing the surface of the diaper that faces the wearer when worn with portions cut away to show underlying features.

Accordingly, the composite web 20 of the present invention can be configured to form front ears 70 and back ears 80 that may suitably be used in connection with an absorbent article, such as the diaper 100. As representatively illustrated in FIGS. 6 and 7, the front ears 70 can include a front ear proximal edge 71, an opposed front ear distal edge 72, a front ear first connecting edge 74 and a front ear second connecting edge 76. The back ears 80 can include a back ear proximal edge 81, an opposed back ear distal edge 82, a back ear first connecting edge 84 and a back ear second connecting edge 86 (FIGS. 5 and 7).

The proximal edges 71, 81 are the portion of the ears 70, 80 that are joined to the diaper 100. The distal edges 72, 82 are those edges of the ears 70 and 80 that are opposite the proximal edges 71, 81 moving in a direction outboard from the diaper 100. The first and second connecting edges 74, 76, 84, 86 connect the proximal edges 71, 81 and the distal edges 72, 82 of the ears 70 and 80.

The proximal edges 71, 81 can further define a proximal edge length. In particular, the back ear proximal edges 81 can define a back ear proximal edge length, indicated by the arrow marked 89, and the front ear proximal edges 71 can define a front ear proximal edge length, indicated by the arrow marked 79. The front ear proximal edge length 79 can be substantially the same as the back ear proximal edge length 89. By "substantially the same proximal edge length" it is meant that the front ear proximal edge length 79 is within 2% of the back ear proximal edge length 89. Suitably, the front ear proximal edge length 79 can be equal to the back ear proximal edge length 89. In particular, since the proximal edge length 79, 89 of the ears 70, 80 are substantially the same, the front ears 70 and the back ears 80 have the same repeat length. As such, as the diaper 100 is being converted, the ears 70 and 80 can all be separated from the composite web 20 simultaneously thereby increasing process efficiency and reducing process equipment and material costs.

The ears 70, 80 can further have a variety of shapes as are known in the art. For example, the back ears 80 can have a complementary shape with each other. Similarly, front ears 70 can also have a complementary shape with each other. Moreover, as the front ears 70 can have complementary shapes with each other, and the back ears 80 can simultaneously have complementary shapes with each other, the front ears 70 can have a different shape than the back ears 80 (FIGS. 1-7). This may be desirable as the front ears 70 may have a different purpose than the back ears 80, or it may be desirable from an aesthetic or material cost perspective. Alternatively, the front ears 70 and back ears 80 may optionally have a substantially similar shape.

The front and/or back ears 70 and/or 80 can also optionally include fastener material 90 from the first and/or the second web of fastener material 32 and/or 34. For example, one of or each of the back ears 80 can include fastener material 90. Optionally, one of or each of the front ears 70 can include fastener material 90.

As mentioned above, the front ears 70 and back ears 80 that can be formed from the composite web 20 of the present invention may suitably be used in connection with the diaper 100. Various materials and methods for constructing diapers are known in the art. For example, suitable diapers are disclosed in U.S. Pat. No. 5,496,298 issued Mar. 5, 1996 to Kuepper et al.; U.S. Pat. No. 4,798,603 issued Jan. 17, 1989, to Meyer et al.; U.S. Pat. No. 5,176,668 issued Jan. 5, 1993, to Bernardin; U.S. Pat. No. 5,192,606 issued Mar. 9, 1993, to Proxmire et ml., and U.S. Pat. No. 5,509,915 issued Apr. 23, 1996, to Hanson et al., each of which are incorporated herein by reference to the extent that they are consistent (i.e., not in conflict) herewith. In particular, absorbent articles including components that can be suitably provided by the composite web 20 of the present invention are described in U.S. patent application Ser. No. 11/116,654, entitled ABSORBENT ARTICLE HAVING FRONT AND BACK EARS, and filed in the name of Van Dyke concurrently with the present application, the entire disclosure of which is hereby incorporated by reference to the extent that it is consistent (i.e., not in conflict) herewith.

For instance, the components can be attached to a disposable diaper 100 representatively illustrated in FIG. 7. The absorbent article 100 defines a front waist region 102, a back waist region 104, and a crotch region 106 connecting the front waist region 102 and the back waist region 104. The absorbent article 100 includes a bodyside liner 110, an outer cover 112, and an absorbent core 114 located between the bodyside liner 110 and the outer cover 112.

The diaper 100 can include various components such as containment flaps 128 and waist elastics 130. Containment flaps 128 are well known in the art and are described in U.S. Pat. No. 4,704,116 issued Nov. 3, 1987, to Enloe, the disclosure of which is hereby incorporated by reference to the extent it is consistent (i.e. not in conflict) with the current disclosure. Waist elastics 130 are described in U.S. Pat. No. 4,916,005 to Lippert et al., the disclosure of which is hereby incorporated by reference to the extent it is consistent (i.e. not in conflict) with the current disclosure.

As described above, the ear fastener material 90 can be included on the back ears 80 and/or the front ears 70. The ear fastener material 90 can be adapted to connect (desirably releasably connect) the front waist region 102 to the back waist region 104 of the diaper 100, so as to fasten the diaper 100 about the waist of the wearer when in use.

Various woven and nonwoven fabrics can be used for the bodyside liner 110. For example, the bodyside liner may be composed of a meltblown or spunbonded web of polyolefin fibers. The outer cover 112 of the diaper 100, may suitably be composed of a material that is liquid impermeable. For example, a typical outer cover can be manufactured from a thin plastic film or other flexible liquid impermeable material. If it is desired to present the outer cover 112 with a more clothlike feeling, the outer cover 112 may comprise a polyethylene film having a nonwoven web laminated to the outer surface thereof, such as a spunbond web of polyolefin fibers. Still further, the outer cover 112 may optionally be composed of a microporous "breathable" material which permits vapors to escape from the absorbent core 114 while still preventing liquid exudates from passing into the outer cover 112. The absorbent core 114 may suitably include a body of cellulosic fibers having superabsorbent material intermixed with the cellulosic fibers.

The ears 70 and 80 may be joined to the diaper in a variety of ways as are known in the art. For example, the ears 70 and 80 may be joined to the diaper 100 with adhesive, ultrasonic bonds, pressure bonds, thermal bonds, and the like, or combinations thereof.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred aspect(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A composite web defining a lateral direction, longitudinal direction, a longitudinal centerline, a first composite web side edge a second composite web side edge opposed to said first composite web side edge, a first planar surface and a second planar surface opposite said first planar surface, said composite web comprising:
    A base web;
    A first web of fastener material disposed on said base web between said first and second composite web side edges and extending in said longitudinal direction;
    A second web of fastener material disposed on said base web between said first and second composite web side edges and extending in said longitudinal direction wherein said second web is laterally spaced from said first web of fastener material;
    A first sinusoidal line of separation extending in said longitudinal direction and passing through said base web; and
    A second sinusoidal line of separation laterally spaced from said first sinusoidal line of separation, extending in said longitudinal direction and passing through said base web, wherein said second sinusoidal line of separation passes through said second web of fastener material and said composite web is configured to form discrete components free from any trim waste.

2. The composite web of claim 1 wherein said first web of fastener material and said second web of fastener material are each disposed on said first planar surface.

3. The composite web of claim 1 wherein said first web of fastener material is disposed on said first planar surface and said second web of fastener material is disposed on said second planar surface.

4. The composite web of claim 1 wherein said first web of fastener material and said second web of fastener material are substantially continuous webs.

5. The composite web of claim 1 wherein at least one of said first sinusoidal line of separation and said second sinusoidal line of separation is a series of perforations.

6. The composite web of claim 1 wherein at least one of said first sinusoidal line of separation and said second sinusoidal line of separation is a continuous cut.

7. The composite web of claim 1 wherein said base web comprises elastomeric material capable of being elongated in said lateral direction.

8. The composite web of claim 1 wherein said base web comprises multiple layers of material.

9. The composite web of claim 1 wherein said first sinusoidal line of separation and said second sinusoidal line of separation are substantially curvilinear.

10. The composite web of claim 1 wherein at least one of said first sinusoidal line of separation or said second sinusoidal line of separation is substantially rectilinear.

11. The composite web of claim 1 further comprising a plurality of interconnecting lines of separation that extend from said first sinusoidal line of separation to said second sinusoidal line of separation.

12. The composite web of claim 11 wherein each of said first sinusoidal line of separation and said second sinusoidal line of separation define a plurality of peak regions and a plurality of trough regions and wherein each of said plurality of interconnecting lines of separation extend from one of said peak regions in said first sinusoidal line of separation to one of said trough regions in said second sinusoidal line of separation.

13. The composite web of claim 1 further comprising a plurality of first outboard lines of separation that extend from said first sinusoidal line of separation away from said longitudinal centerline to said first composite web side edge and a plurality of second outboard lines of separation that extend from said second sinusoidal line of separation away from said longitudinal centerline to said second composite web side edge.

14. The composite web of claim 1 wherein said composite web is configured to form multiple components and wherein said multiple components have the same repeat length.

15. The composite web of claim 1 further comprising a dividing line of separation located between the first sinusoidal line of separation and the second sinusoidal line of separation.

16. A Composite web defining a lateral direction, a longitudinal direction and a longitudinal centerline, said composite web comprising:
    A base web;
    A first web of fastener material disposed on said base web;
    A second web of fastener material disposed on said base web;
    A first sinusoidal line of separation passing through said base web;
    A second sinusoidal line of separation passing through said base web;
    A plurality of interconnecting lines of separation that extend from said first sinusoidal line of separation to said second sinusoidal line of separation and pass through said base web;

A plurality of first outboard lines of separation that extend from said first sinusoidal line of separation away from said longitudinal centerline; and A plurality of second outboard lines of separation that extend from said second sinusoidal line of separation away from said longitudinal centerline;

Wherein said first sinusoidal line of separation gasses through said first web of fastener material and said second sinusoidal line of separation passes through said second web of fastener material and wherein said first sinusoidal line of separation, said second sinusoidal line of separation, said plurality of interconnecting lines of separation, said first outboard lines of separation and said second outboard lines of separation are configured to form discrete components from said composite web free from any trim waste.

17. The composite web of claim 16 wherein said first sinusoidal line of separation and said second sinusoidal line of separation are curvilinear.

18. The composite web of claim 16 wherein at least one of said first sinusoidal line of separation or said second sinusoidal line of separation is rectilinear.

19. The composite web of claim 16 wherein said composite web is configured to form multiple components and wherein said multiple components have the same repeat length.

20. The composite web of claim 16 further comprising a dividing line of separation located between the first sinusoidal line of separation and the second sinusoidal line of separation.

* * * * *